(12) United States Patent
Stenfors

(10) Patent No.: US 7,014,360 B2
(45) Date of Patent: Mar. 21, 2006

(54) X-RAY EXAMINATION APPARATUS

(75) Inventor: Per Stenfors, Stocksund (SE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/966,753

(22) Filed: Oct. 15, 2004

(65) Prior Publication Data

US 2005/0117711 A1    Jun. 2, 2005

(30) Foreign Application Priority Data

Oct. 17, 2003    (EP) .................................. 03023642

(51) Int. Cl.
*H05G 1/02*    (2006.01)
(52) U.S. Cl. ...................... 378/195; 378/196; 378/197
(58) Field of Classification Search ................ 378/193, 378/194, 195, 196, 197; 74/89.2, 89.21, 74/89.22
See application file for complete search history.

(56) References Cited

U.S. PATENT DOCUMENTS 6,364,525 B1 *  4/2002  Mellstrom et al. .......... 378/197

* cited by examiner

*Primary Examiner*—Edward J. Glick
*Assistant Examiner*—Courtney Thomas

(57) ABSTRACT

An x-ray examination apparatus (1) comprising a fixed part (2) and a carriage (3) mounted to be vertically movable relative to said fixed part (2), said carriage (3) having a horizontally projecting shaft (4), an x-ray apparatus component (5) being rotatably mounted on said shaft (4) and vertically movable together with said carriage (3), wherein a central cogwheel (6) is arranged on said shaft (4), said cogwheel (6) is meshing with two smaller cogwheels (7, 8) which are arranged on both sides of said central cogwheel (6) on said carriage (3), each of said smaller cog-wheels (7, 8) encompasses a cog or chain wheel (9, 10), a connector is, in succession, entrained around the upper sides of said cogs or chain wheels (9, 10) and partially entraining a lower wheel and partially en-training an upper wheel, said wheels are arranged on the fixed part (2), said connector partially entraining the lower sides of said cogs or chain wheels (9, 10), and either the lower wheels or the upper wheels are deflection wheels (12, 13) and the others are drive wheels (14, 15) of the connector.

17 Claims, 3 Drawing Sheets

X-RAY EXAMINATION APPARATUS

CROSS REFERENCE TO RELATED APPLICATIONS

This application claims priority to the European application No. 03023642.6, filed Oct. 17, 2003 and which is incorporated by reference herein in its entirety.

FIELD OF INVENTION

The present invention relates to an x-ray examination apparatus, comprising a fixed part and a carriage mounted to be vertically movable relative to said fixed part, said carriage having a horizontally projecting shaft, an x-ray imaging component being rotatably mounted on said shaft and vertically movable together with said carriage.

BACKGROUND OF INVENTION

In x-ray examination apparatus of this type the shaft is normally connected with apparatus components like a patient table, a C-arm support with an x-ray tube and a radiation detector.

An x-ray examination apparatus of the above type is known from EP-A-1 059 065. This apparatus comprises a lifting and rotating device comprising a pulley with a disk, having a peripheral surface which is at least partially circular and a connector, which can be a chain or a belt which is entrained around deflection wheels and drive wheels. When the drive wheels are simultaneously rotated in a different direction the x-ray apparatus component and the carriage are vertically moved and when the drive wheels are simultaneously rotated in a same direction the x-ray apparatus component rotates around the centre of the shaft.

SUMMARY OF INVENTION

However, it is disadvantageous that in practical use the diameter of the disk must be about 1,2 m. Therefore there exists a need for an x-ray examination apparatus which is smaller and more compact. Unfortunately, it is not possible to replace the disk with an ordinary gear train, because this would introduce unwanted play or clearance into the system.

It is therefore an object of the present invention to provide an x-ray examination apparatus which has a smaller size and maintains stable during a movement.

According to the present invention, this object is achieved by the claims.

According to the invention two identical gear reductions are used, which divide the load. In this way unwanted play is prevented because the smaller cogwheels are always under tension against the same tooth flank. As a result a central cogwheel can be used with a diameter of approximately 40 cm, so that the apparatus according to the invention is considerably smaller compared to conventional devices.

According to the invention each of the smaller cogwheels is connected to a cog or chain wheel on which the connector is lead. Even if the connector fails, the x-ray examination apparatus is safe because the meshing cogwheels prevent any movement.

According to an exemplary embodiment of the invention the connector can be a chain or a belt, in particular a toothed belt. Further it is preferred that the connector is endless, i.e. an endless chain or an endless tooth belt.

According to another aspect of the present invention the smaller cog-wheels are of equal size. The smaller cogwheels can be arranged below the central cogwheel, at its left and right hand side. It is preferred that the smaller cogwheels are arranged at the same height.

According to an advantageous development of the present invention the reduction ratio of the cogwheel and the smaller cogwheels is about 1:3 or 1:4. With this embodiment it is possible to create an x-ray examination apparatus which has a very small size and shows no play when it is moved.

The lower wheels are preferably deflection wheels and the upper wheels are preferably drive wheels. However, in a different embodiment the positions of the deflection wheels and the drive wheels can be exchanged.

BRIEF DESCRIPTION OF THE DRAWINGS

The invention and its underlying principle will be better understood when consideration is given to the following detailed description of a preferred embodiment.

DETAILED DESCRIPTION OF INVENTION

Figure 1:
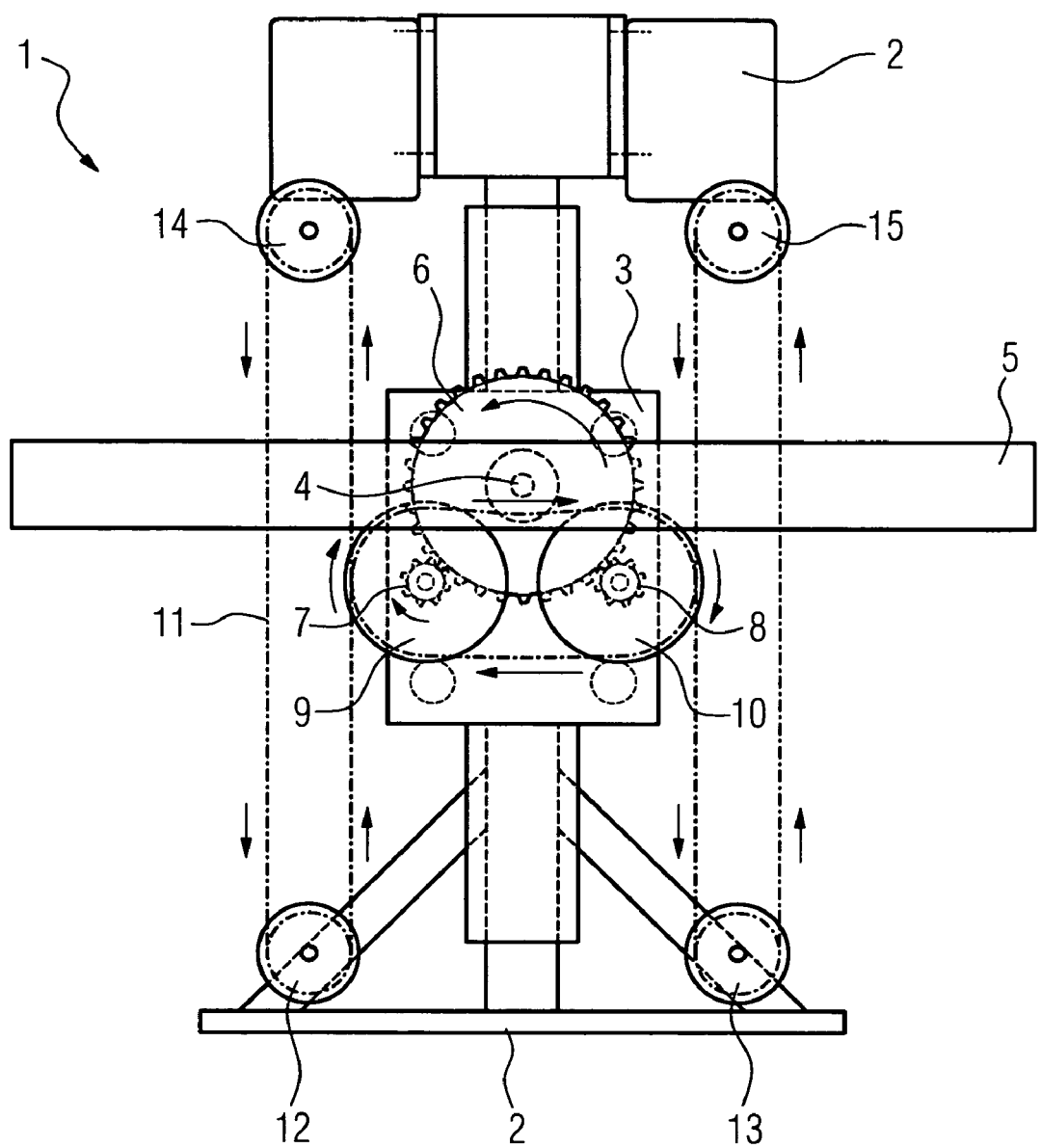
FIG. 1 is a schematic front view of an x-ray examination apparatus according to the present invention.

In FIG. 1 an x-ray examination apparatus 1 is shown, comprising a fixed part 2 and a carriage 3, mounted to be vertically movably relative to the fixed part 2. The vertical movement is achieved using known means, e.g. a worm drive and therefore not shown in more detail.

The carriage 3 has a horizontally projecting shaft 4 on which an x-ray apparatus component 5 is mounted. The x-ray apparatus component 5 is shown schematically in FIG. 1 and may further encompass a patient table, a C-arm support with an x-ray tube and a radiation detector.

A central cogwheel 6 is arranged on the shaft 4 and fixed at the carriage 3, so that the cogwheel 6 and the x-ray apparatus component 5 are vertically moved together with the carriage 3.

The central cogwheel 6 is meshing with two smaller cogwheels which are arranged on the carriage 3 in the plane of the central cogwheel 6. The smaller cogwheels 7, 8 are arranged symmetrically on both sides underneath the central cogwheel 6.

From FIG. 1 it can be seen that the smaller cogwheels 7, 8 encompass chain wheels 9, 10, which are respectively connected to the smaller cog-wheels 7, 8 through a common shaft. The diameter of the disk-like chain wheels 9, 10 is substantially larger than the diameter of the smaller cogwheels 7, 8.

An endless connector in the form of a chain 11 is entrained around the upper sides of the chain wheels 9, 10 and partially entraining lower wheels, which are formed as deflection wheels 12, 13. From the deflection wheels 12, 13 the chain 11 is lead substantially vertically upward to drive wheels 14, 15. The drive wheels 14, 15 are connected to electric motors 16 to cause a movement of the chain 11, the carriage 3 and the x-ray apparatus component 5. From the drive wheels 14, 15 the chain 11 is further lead to the lower sides of the chain wheels 9, 10. As can be seen from FIG. 1 the route of the chain 11 in the x-ray examination apparatus 1 is symmetrical about a vertical axis.

When the drive wheels 14, 15 are rotated in the same direction, as indicated by the arrows, the central cogwheel 6 is caused to rotate counter-clockwise by the smaller cogwheels 7, 8, which are connected to the chain wheels 9, 10 and the chain 11.

When the drive wheels 14, 15 are rotated simultaneously in different directions the central cogwheel 6 is not rotated but the carriage 3 and the x-ray apparatus component 5 are moved vertically upward or downward, de-pending on the direction of rotation of the drive wheels 14, 15.

Figure 2:
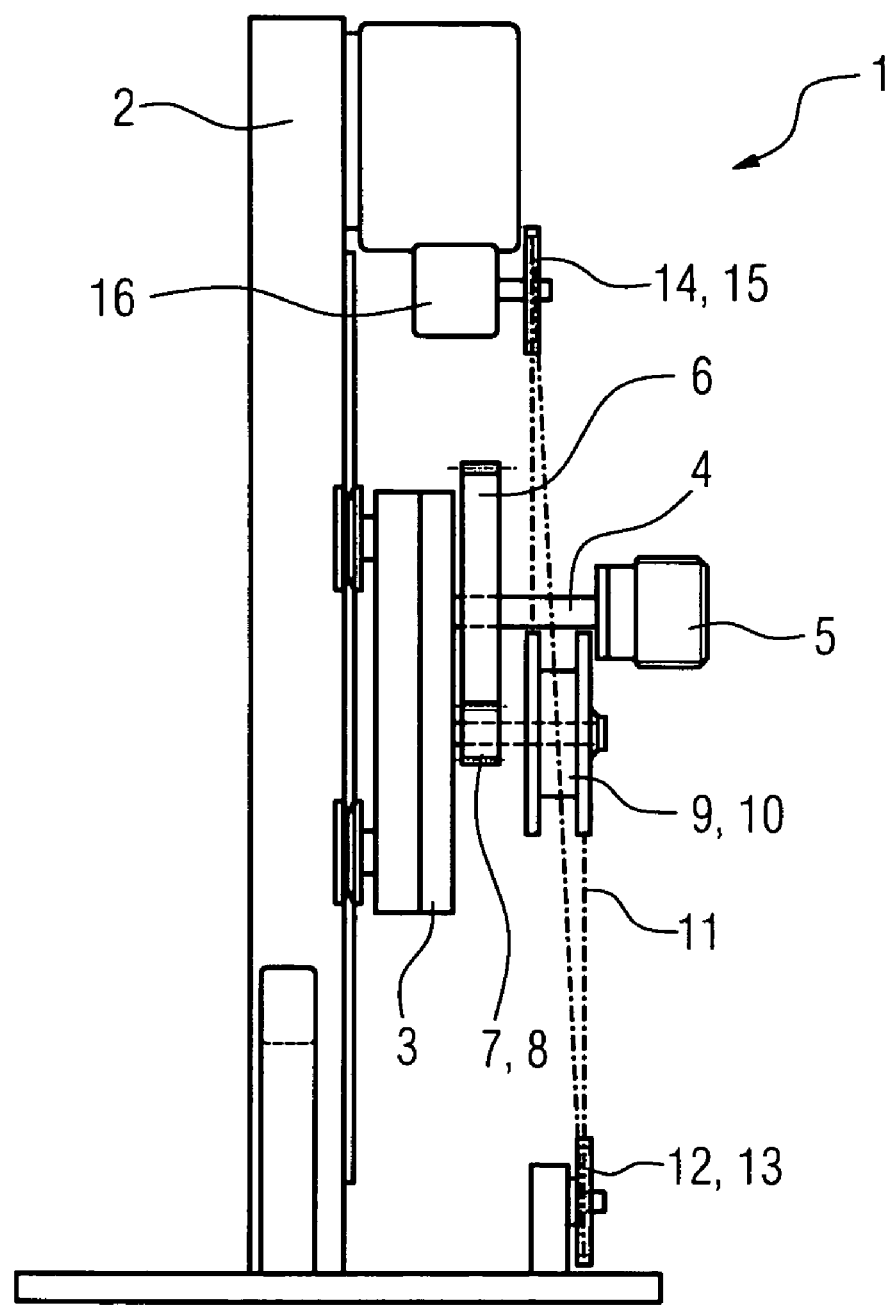
FIG. 2 is a schematic side view of the x-ray examination apparatus of FIG. 1.

FIG. 2 is a schematic side view of the x-ray examination apparatus of FIG. 1.

In FIG. 2 it can be seen that the cogwheels 6, 7, 8 are on one side of the plane of the chain 11 and the x-ray apparatus component 5 is on the other side of this plane. Further it is visible that the smaller cog-wheels 7, 8 are connected to the chain wheels 9, 10 by respective shafts.

In the present invention the diameter of the central cogwheel 6 can be approximately 40 cm and the reduction ratio of the cogwheels can be in the range 1:3 or 1:4.

Figure 3:
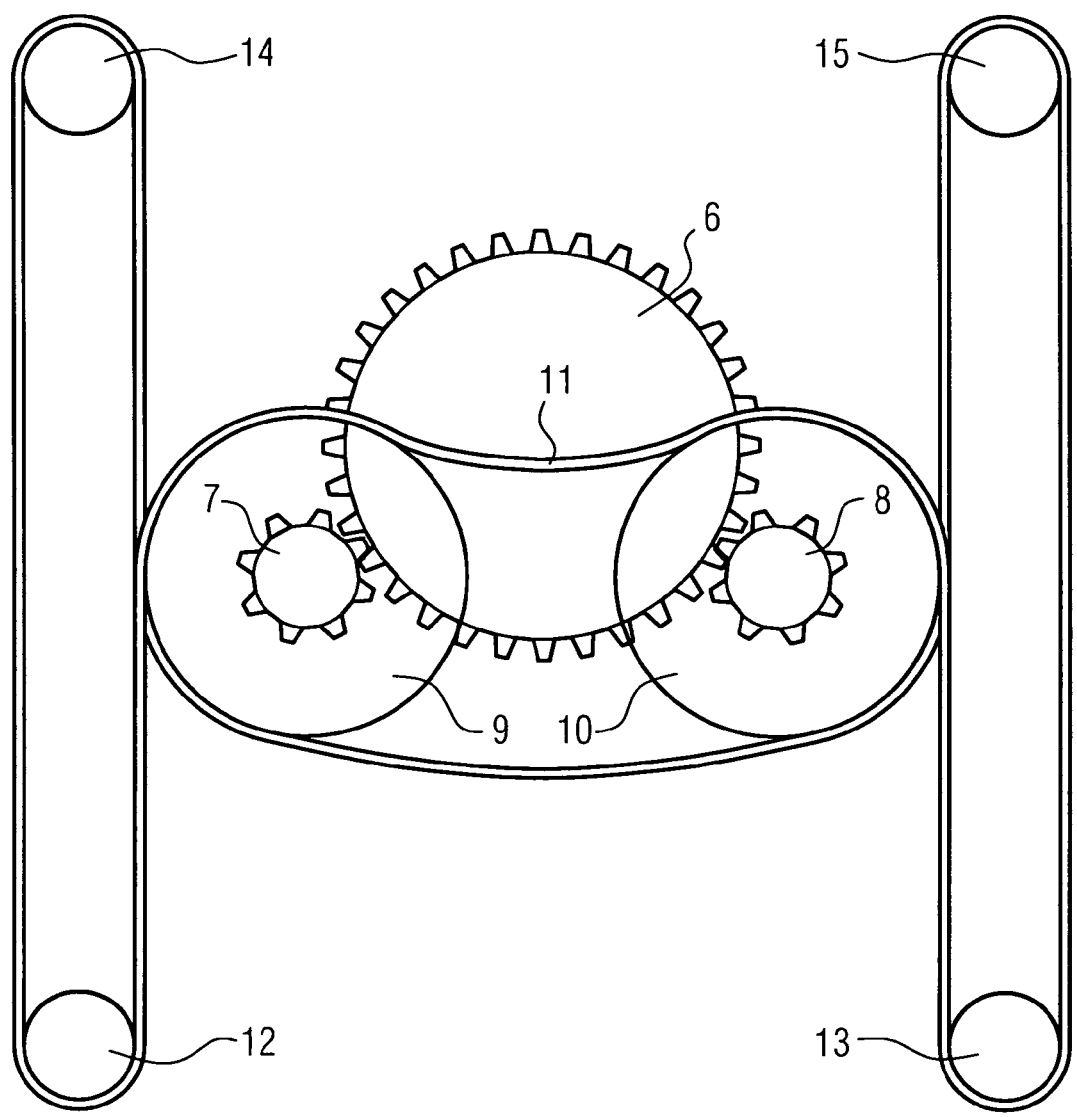
FIG. 3 shows the connector and the cogwheels of the x-ray examination apparatus according to the present invention in an enlarged scale.

FIG. 3 shows the chain 11 and the cogwheels 6, 7, 8 in an enlarged scale.

The endless chain 11 runs from the upper side of chain wheel 9 downward to the deflection wheel 13, upward to drive wheel 15, downward to the lower side of chain wheel 10, further to the lower side of chain wheel 9, upward to drive wheel 14, downward to deflection wheel 12 and upward to the upper side of chain wheel 9. As can be seen in FIG. 3 the chain is not under tension between the chain wheels 9, 10. In case a cog flank brakes only very small movements are possible between the cogwheels 6, 7, 8 due to play. However, large movements of the carriage 3 and the other moveable parts are prevented by the meshing gears 6, 7, 8.

What is claimed is:

1. An x-ray examination apparatus, comprising:
   a fixed part;
   a carriage vertically movable relative to the fixed part, the carriage having a horizontally projecting shaft;
   a rotatable x-ray apparatus component arranged on the shaft and vertically movable together with the carriage;
   a first central cogwheel arranged on the shaft;
   a second and a third cogwheel arranged on the carriage in mesh with the first cogwheel, the second cogwheel arranged on a left side relative to the central cogwheel and the third cogwheel arranged on a right side relative to the cogwheel, and the second and third cogwheel including a first and second cog respectively or a first and second chain wheel respectively; and
   a connector adapted to consecutively entrain:
   upper sides of the first and second cogs or the first and second chain wheels respectively;
   a lower wheel arranged on the fixed part;
   an upper wheel arranged on the fixed part; and
   lower sides of the first and second cogs or first and second chain wheels respectively.

2. The x-ray examination apparatus according to claim 1, wherein the connector partially entrains the lower and upper wheels.

3. The x-ray examination apparatus according to claim 1, wherein the connector partially entrains the lower sides of the first and second cogs or chain wheels respectively.

4. The x-ray examination apparatus according to claim 1, wherein the lower wheel is a drive wheel driving the connector and the upper wheel is a deflection roller for turning round the connector.

5. The x-ray examination apparatus according to claim 1, wherein the upper wheel is a drive wheel driving the connector and the lower wheel is a deflection roller for turning round the connector.

6. The x-ray examination apparatus according to claim 1, wherein the connector is a chain.

7. The x-ray examination apparatus according to claim 1, wherein the connector is a belt.

8. The x-ray examination apparatus according to claim 7, wherein the belt is a toothed belt.

9. The x-ray examination apparatus according to claim 1, wherein the connector is endless.

10. The x-ray examination apparatus according to claim 1, wherein the second and third cogwheels are smaller than the first cogwheel.

11. The x-ray examination apparatus according to claim 1, wherein the second and third cogwheels are of equal size.

12. The x-ray examination apparatus according to claim 1, wherein the second and third cogwheels are arranged at the same height relative to a ground level on which a base plate of the apparatus is arranged.

13. The x-ray examination apparatus according to claim 1, wherein a first transmission ratio from the first to the second cogwheel is taken from the range between 1:3 and 1:4.

14. The x-ray examination apparatus according to claim 1, wherein a second transmission ratio from the first to the third cogwheel is taken from the range between 1:3 and 1:4.

15. The x-ray examination apparatus according to claim 1, comprising at least two lower wheels used as deflection rollers for turning round the connector and at least two upper wheels used as drive wheels for driving the connector.

16. The x-ray examination apparatus according to claim 15, wherein the drive wheels rotate simultaneously in different rotating directions to move the carriage and the x-ray apparatus component vertically.

17. The x-ray examination apparatus according to claim 15, wherein the drive wheels rotate simultaneously in the same rotating direction to rotate the carriage and the x-ray apparatus component around a longitudinal axis of the shaft.

* * * * *